(12) United States Patent
Gruteser et al.

(10) Patent No.: US 11,497,393 B2
(45) Date of Patent: Nov. 15, 2022

(54) LARYNGO-PHARYNGOSCOPE RETRACTOR SYSTEM

(71) Applicant: OLYMPUS WINTER & IBE GmbH, Hamburg (DE)

(72) Inventors: Thomas Gruteser, Schwarzenbek (DE); Lena Wilker, Hamburg (DE); Katrin Mrotzeck, Luebeck (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 98 days.

(21) Appl. No.: 16/977,977

(22) PCT Filed: Mar. 4, 2019

(86) PCT No.: PCT/EP2019/055245
§ 371 (c)(1),
(2) Date: Sep. 3, 2020

(87) PCT Pub. No.: WO2019/170570
PCT Pub. Date: Sep. 12, 2019

(65) Prior Publication Data
US 2021/0052154 A1 Feb. 25, 2021

(30) Foreign Application Priority Data
Mar. 5, 2018 (DE) .............................. 2018104966.8

(51) Int. Cl.
*A61B 1/267* (2006.01)
*A61B 90/92* (2016.01)
(Continued)

(52) U.S. Cl.
CPC ................ *A61B 1/267* (2013.01); *A61B 1/32* (2013.01); *A61B 17/0206* (2013.01);
(Continued)

(58) Field of Classification Search
CPC .. A61B 1/24; A61B 1/267; A61B 1/32; A61B 2017/00482; A61B 17/0206;
(Continued)

(56) References Cited

U.S. PATENT DOCUMENTS 7,887,483 B2 * 2/2011 Rosenberg ............... A61B 1/24
600/233
9,339,176 B2 * 5/2016 Weinstein ................ A61B 1/32
(Continued)

FOREIGN PATENT DOCUMENTS

| DE | 9420565 U1 | 2/1995 |
| DE | 102010026550 A1 | 1/2012 |
| DE | 102011115077 A1 | 3/2013 |

OTHER PUBLICATIONS

International Search Report dated Jun. 11, 2019 issued in PCT/EP2019/055245.

*Primary Examiner* — Larry E Waggle, Jr.
(74) *Attorney, Agent, or Firm* — Scully, Scott, Murphy & Presser, P.C.

(57) ABSTRACT

A laryngopharyngoscope retractor system including: a plurality of components including: a base frame with a coupling region and a spatula holder that is adjustable in terms of position and orientation by way of adjusting screws; a spatula that is releasably fastenable in the spatula holder; two cheek holder adapters that are releasably fastenable to the base frame; and two cheek holders, each of which is releasably fastenable to a respective cheek holder adapter, wherein one or more of the base frame, the spatula holder, the spatula, the cheek holder adapter and the cheek holder, in the respective regions provided for the releasable connection to another one of the plurality of components have a visible unique code that corresponds to the corresponding regions on the other of the plurality of components.

6 Claims, 5 Drawing Sheets

(51) Int. Cl.
  *A61B 90/94* (2016.01)
  *A61B 1/32* (2006.01)
  *A61B 17/02* (2006.01)
  *A61B 17/29* (2006.01)
  *A61B 90/00* (2016.01)

(52) U.S. Cl.
  CPC .............. *A61B 17/29* (2013.01); *A61B 90/92* (2016.02); *A61B 90/94* (2016.02); *A61B 2090/0808* (2016.02); *A61B 2217/005* (2013.01)

(58) Field of Classification Search
  CPC ................ A61B 17/0293; A61B 17/24; A61B 2090/0808; A61B 90/92; A61B 90/94
  See application file for complete search history.

(56) References Cited

U.S. PATENT DOCUMENTS

| | | | |
|---|---|---|---|
| 9,517,333 B2* | 12/2016 | North | A61B 90/90 |
| 9,724,092 B2* | 8/2017 | Baxter, III | A61B 17/07207 |
| 2010/0217085 A1 | 8/2010 | Williams et al. | |
| 2010/0274093 A1 | 10/2010 | Shelton, IV | |
| 2013/0261401 A1 | 10/2013 | Hawkins et al. | |
| 2014/0229009 A1 | 8/2014 | Froehlich et al. | |
| 2016/0331223 A1* | 11/2016 | Imai | A61B 1/32 |
| 2017/0311940 A1 | 11/2017 | Daavettila et al. | |

\* cited by examiner

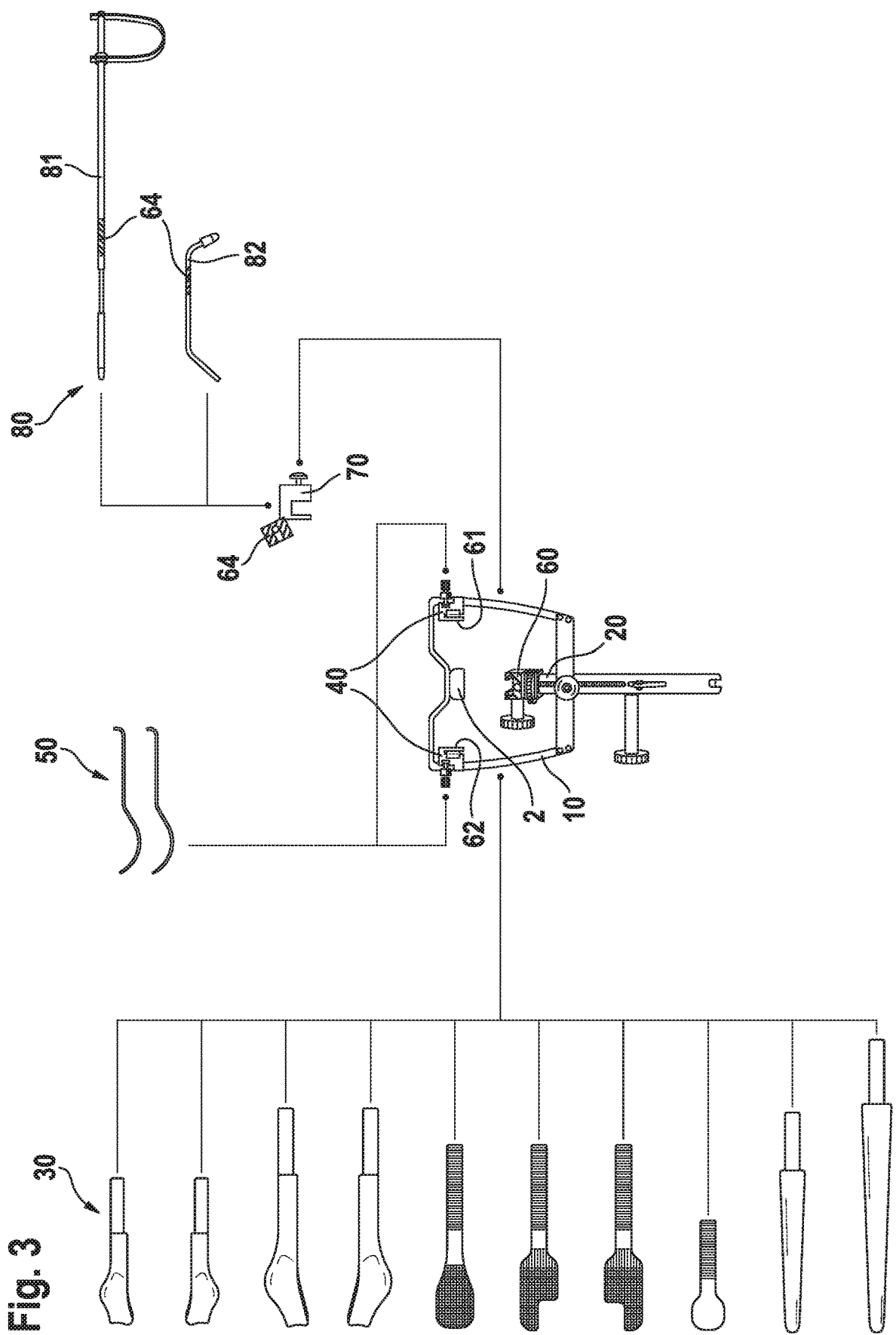

LARYNGO-PHARYNGOSCOPE RETRACTOR SYSTEM

CROSS-REFERENCE TO RELATED APPLICATIONS

The present application is based upon and claims the benefit of priority from PCT/EP2019/055245 filed on Mar. 4, 2019, which claims benefit to DE 10 2018 104 966.8 filed on Mar. 5, 2018, the entire contents of each of which are incorporated herein by reference.

BACKGROUND

Field

The present disclosure relates to a laryngopharyngoscope retractor system.

Prior Art

To examine and perform minimally invasive operations on the pharynx, the larynx and/or the upper aerodigestive tract of a patient, it is known to insert a laryngoscope or pharyngoscope through the mouth of the patient to the examination or operation site in order to obtain an appropriate view of the examination or operation site. Additionally, instruments required for the examination or operation can be guided accordingly through the mouth of the patient.

The use of so-called laryngopharyngoscope retractors is known for transoral, robot-assisted surgery (TORS) or conventional microsurgery, for example on the larynx or on the base of the tongue, and for laser surgery on the upper aerodigestive tract. With the help of these retractors, the mouth of the patient can be kept open during the examination or operation and the tongue and surrounding tissue can be kept aside at the same time.

By way of example, a corresponding laryngopharyngoscope retractor is disclosed in document US 2016/0331223 A1. The retractor comprises a rigid frame, a maxillary spoon being fastened to the upper bar thereof and a spatula holder that is adjustable in terms of position and orientation being arranged at the lower bar thereof. With a suitable spatula inserted therein, the retractor can be braced between maxilla and mandible of the patient such that the retractor keeps the mouth open and, at the same time, keeps the tongue and possibly further tissue aside using the spatula. Additionally, cheek holders can be fastened to the two lateral struts of the frame and be used to pull apart the cheeks of the patient in order to increase the mouth opening.

Laryngopharyngoscope retractors are capable of being disassembled to a great extent, inter alia for cleaning purposes. However, it was found that reassembling corresponding retractors is not straightforward on account of the multiplicity of components and regularly does not succeed without detailed instructions.

SUMMARY

It is an object to develop a laryngopharyngoscope retractor system which no longer has the disadvantages known from the prior art or at least only still has these to a reduced extent.

Accordingly, a laryngopharyngoscope retractor system is provided. The laryngopharyngoscope retractor system comprising:

a base frame with a coupling region and a spatula holder that is adjustable in terms of position and orientation by way of adjusting screws;

a spatula that is releasably fastenable in the spatula holder;

two cheek holder adapters that are releasably fastenable to the base frame; and two cheek holders, each of which is releasably fastenable to a respective cheek holder adapter, wherein the base frame, the spatula holder, the spatula, the cheek holder adapter and/or cheek holder, in the respective regions provided for the releasable connection to one of the other components, have a visible unique code that corresponds to the corresponding regions on the other component.

Such laryngopharyngoscope retractor system is based on the discovery that a laryngopharyngoscope retractor system cannot have unique, precisely fitting shapes of the components to be connected to one another, which only allow a "correct" assembly and are quite common in other disassemblable medical devices, on account of the required variability of the arrangement of individual components on the base frame in this case. By way of example, the spatula, the cheek holder adapter and the cheek holder must be fastenable to the spatula holder, the base frame and the cheek holder adapter in such a flexible fashion in terms of relative position and/or orientation that precisely fitting shapes in the connecting regions of the aforementioned components, which generally mean a restriction of the flexibility of attachment to only one degree of freedom, are not possible.

To nevertheless facilitate a simple assembly of the laryngopharyngoscope retractor system which can require no detailed instructions, visible codes are provided on the individual components. These codes are found in those regions of the individual components where another component can be or should be detachably connected in each case. Since components to be interconnected have mutually identical codes, an immediate assignment of the individual components to one another and a fast and unique identification of the interacting connection regions provided are possible. The laryngopharyngoscope retractor system can thus be quickly and easily correctly assembled without detailed instructions, purely on account of the code provided.

Here, the code can be alphanumeric, the code can be a single digit only. Thus, the code could consist of a single letter or numeral, for example, which is arranged in the region of the respective regions provided for connection purposes. Here, the code can be provided in such a way that the alignment of the code is identical on the two components to be connected in the case of the correct assembly.

Alternatively, a color code can be provided as the code, in which the regions of the components provided for the mutual connection are colored in identical fashion. Thus, an assignment of the individual colors of the connecting regions can ensure a correct assembly of the laryngopharyngoscope retractor system. In cases where a component can be fastened to another component in more than one orientation as a matter of principle, the components can each have two differently colored codes such that the correct orientation is obtained when the two codes correspond at the same time.

The laryngopharyngoscope retractor system can furthermore comprise at least one auxiliary means adapter that is releasably fastenable to the base frame and at least one auxiliary means that is fastenable to an auxiliary means adapter, wherein each auxiliary means, in the region provided for the releasable connection, has a visible code corresponding to the corresponding regions on at least one auxiliary means adapter. The auxiliary means and the auxiliary means adapter thus can be encoded in a manner analogous to the components of the laryngopharyngoscope retractor system already discussed above. Therefore, reference is made to the statements given above in respect of further explanation and alternative embodiments of the code for the auxiliary means and the auxiliary means adapters. The at least one auxiliary means can be a light carrier, a tumor grasping forceps, a suction tube (for liquids) and/or a smoke suction tube.

An auxiliary means adapter could be provided for use with various auxiliary means, wherein the auxiliary means fitting to the auxiliary means adapter each have an identical code in the regions provided for the connection to the auxiliary means adapter. Expressed differently, two different auxiliary means could have identical codes; this indicates that they can be fastened to the same auxiliary means adapter.

The laryngopharyngoscope retractor system can comprise additional spatulas, cheek holders and/or auxiliary means for optional exchange. By way of example, different Weinstein-O'Malley spatulas, tongue depressors, laryngeal spatulas and mandibular spatulas, each in different sizes and/or configurations, can be provided; depending on the intended examination or operation, these are releasably fastened in the spatula holder of the laryngopharyngoscope retractor system.

BRIEF DESCRIPTION OF THE DRAWINGS

The embodiments will now be described in exemplary fashion, with reference being made to the attached drawings. In detail:

FIG. 3 illustrates a third laryngopharyngoscope retractor system.

DETAILED DESCRIPTION

Figure 1A:
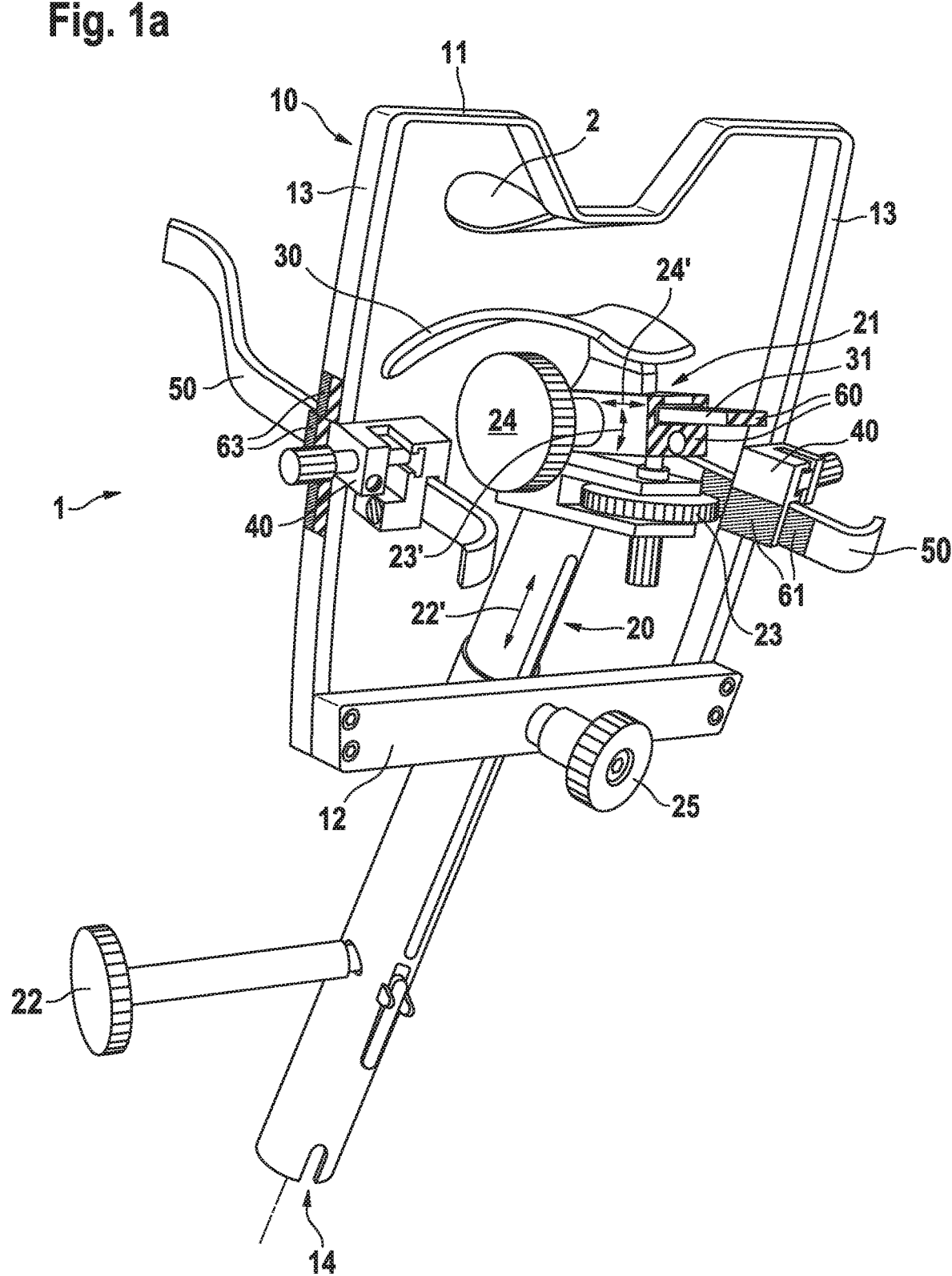
FIGS. 1a and 1b illustrate show a first laryngopharyngoscope retractor system.
Figure 1B:
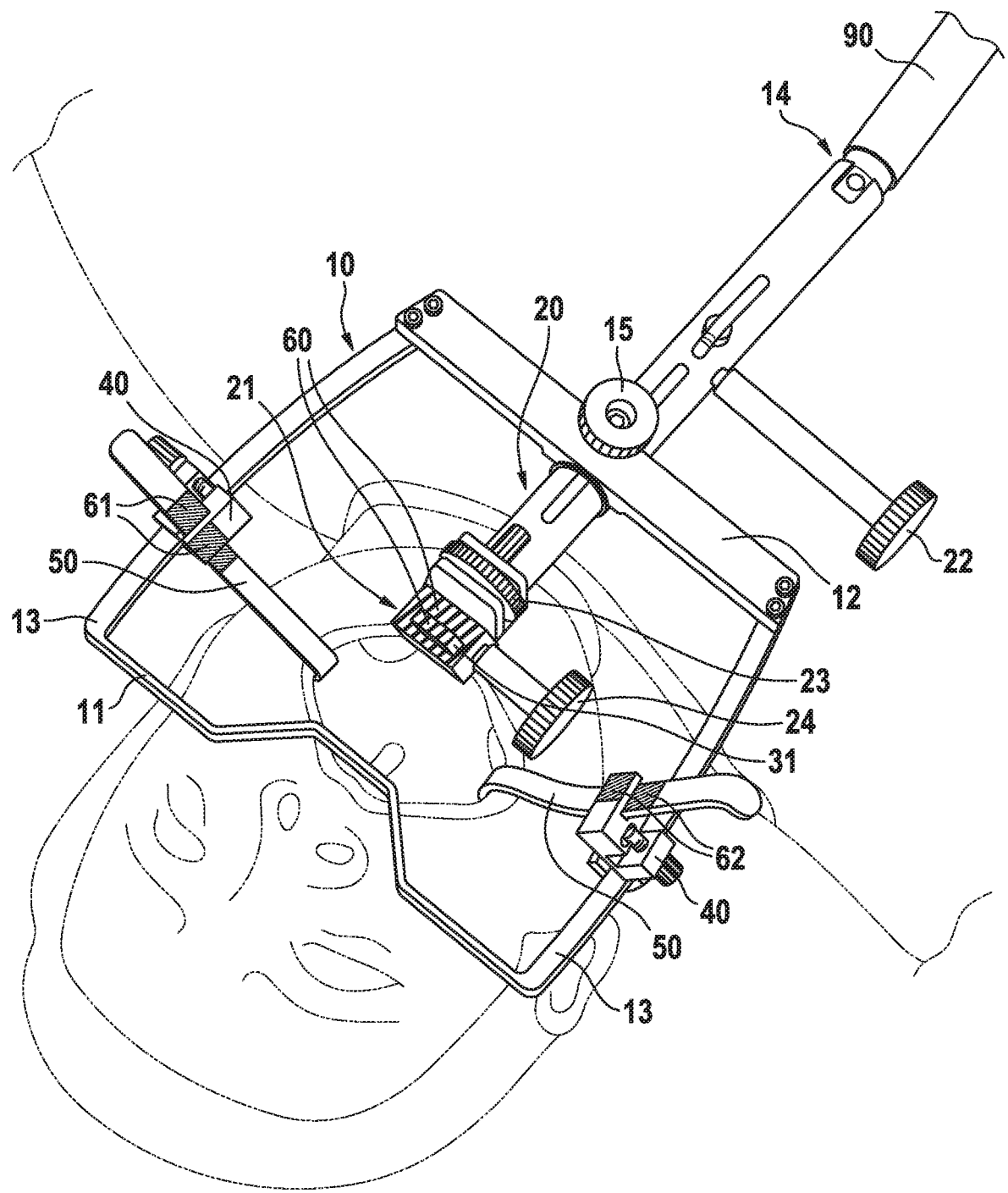

FIGS. 1a and 1b illustrate a first exemplary embodiment of a laryngopharyngoscope retractor system 1.

The laryngopharyngoscope retractor system 1 comprises a base frame 10, a maxillary spoon 2 being arranged at the upper bar 11 thereof. A spatula holder 20 is arranged at the lower bar 12 and has inserted therein a spatula 30 with its connecting piece 31 provided therefor. The actual receiving region 21 of the spatula holder 20 is adjustable in terms of position and orientation by way of the adjusting screws 22, 23. The position of the spatula 30 in the spatula holder 20 itself can be altered by the adjusting screw 24. The adjustability achievable by the individual adjusting screws 22, 23, 24 is indicated by the double-headed arrows 22', 23', 24', wherein an unwanted movement in the direction of the arrow 22' can be prevented by the locking screw 25.

Furthermore, two cheek holder adapters 40 are releasably fastened to the two struts 13 of the base frame 10. The cheek holder adapters 40 can be fastened to the struts 13 at any position. One cheek holder 50 is releasably attached to each cheek holder adapter 40 at a position that is able to be chosen freely.

A coupling region 14, by means of which the base frame 11 can be fastened to a joint holder 90 (cf. FIG. 1b), for example, is provided at the distant end of the spatula holder 20.

The ultimate use of the laryngopharyngoscope retractor system 1 for examination or operation purposes is illustrated in FIG. 1b and such use is known from the prior art.

Various codes 60-63 in the form of color codes are provided at the individual components 10, 20, 30, 40, 50 of the laryngopharyngoscope retractor system 1, to be precise in those regions, in each case, in which two components 10, 20, 30, 40, 50 should be releasably interconnected.

Thus, the spatula holder 20 and the connecting piece 31 of the spatula 30 have a first unique color code 60 on a respective surface, in such a way that a continuous area with the same color arises in a plan view (cf. FIG. 1b). An analogous statement also applies to the connecting regions between cheek holder adapter 40 and cheek holder 50, which each have a color code 61, 62 that deviates from the first color code 60, with the color codes 61, 62 of the left and right cheek holder adapters 40 and cheek holders 50 also differing (cf. FIG. 1b).

A color code 63 with two different colors is provided in the connecting region between base frame 10 and cheek holder adapter 40. The two different color fields are arranged in such a way that they can only be brought into correspondence at the same time in the case of a correct orientation of the cheek holder adapter 40 in relation to the base frame 10. The corresponding color code for the other, right cheek holder adapter 40 (not illustrated) likewise comprises two different colors; these are arranged analogously in two color fields but differ from the colors of the left cheek holder adapter 40. This can ensure that the cheek holder adapters 40 are mounted on the correct side of the base frame 10 in each case. If the two cheek holder adapters 40 can be fastened as desired to one of the two struts 13, the color code 63 on the cheek holder adapters 40 can also be identical.

Figure 2A:
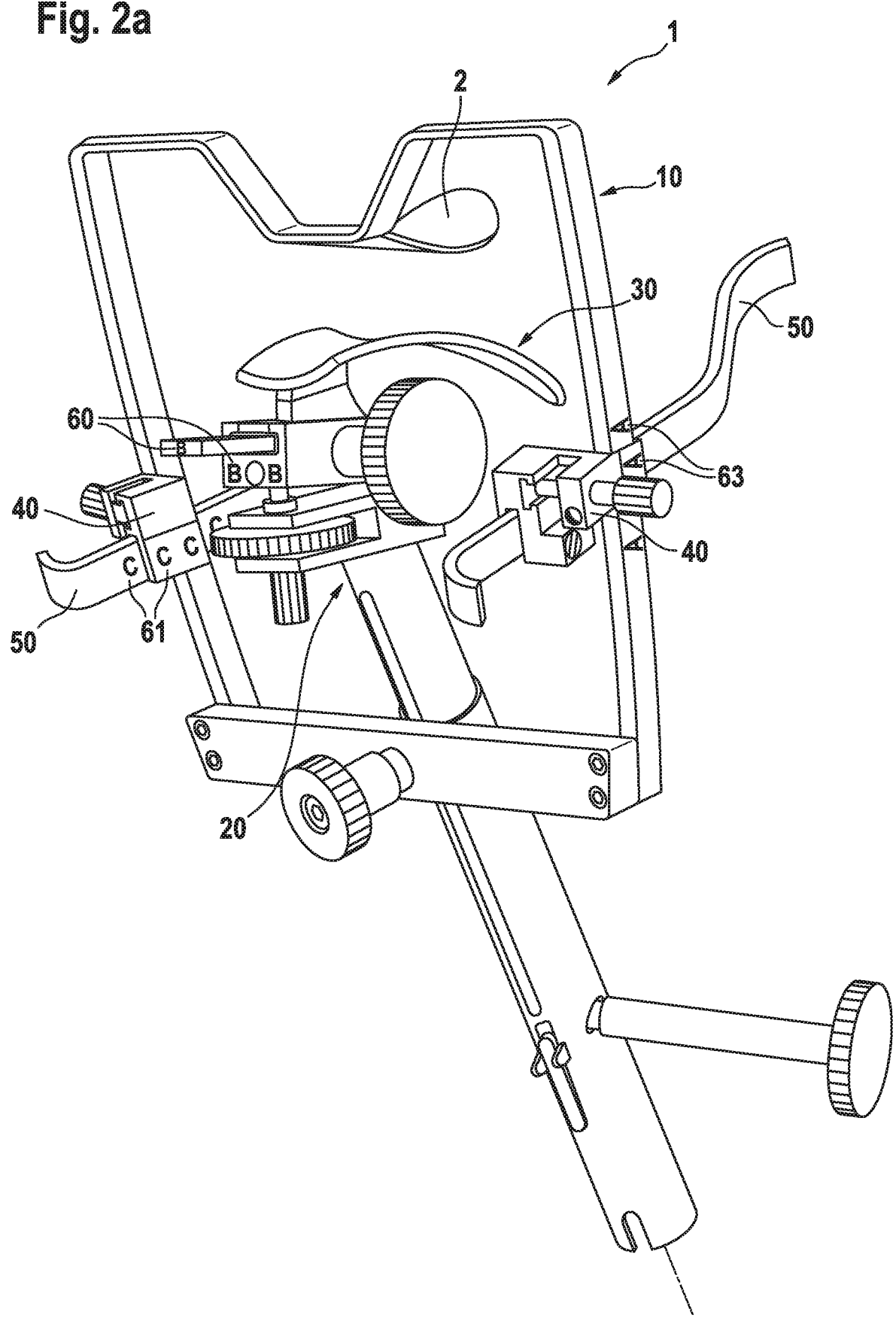
FIGS. 2a and 2b illustrate a second laryngopharyngoscope retractor system.
Figure 2B:
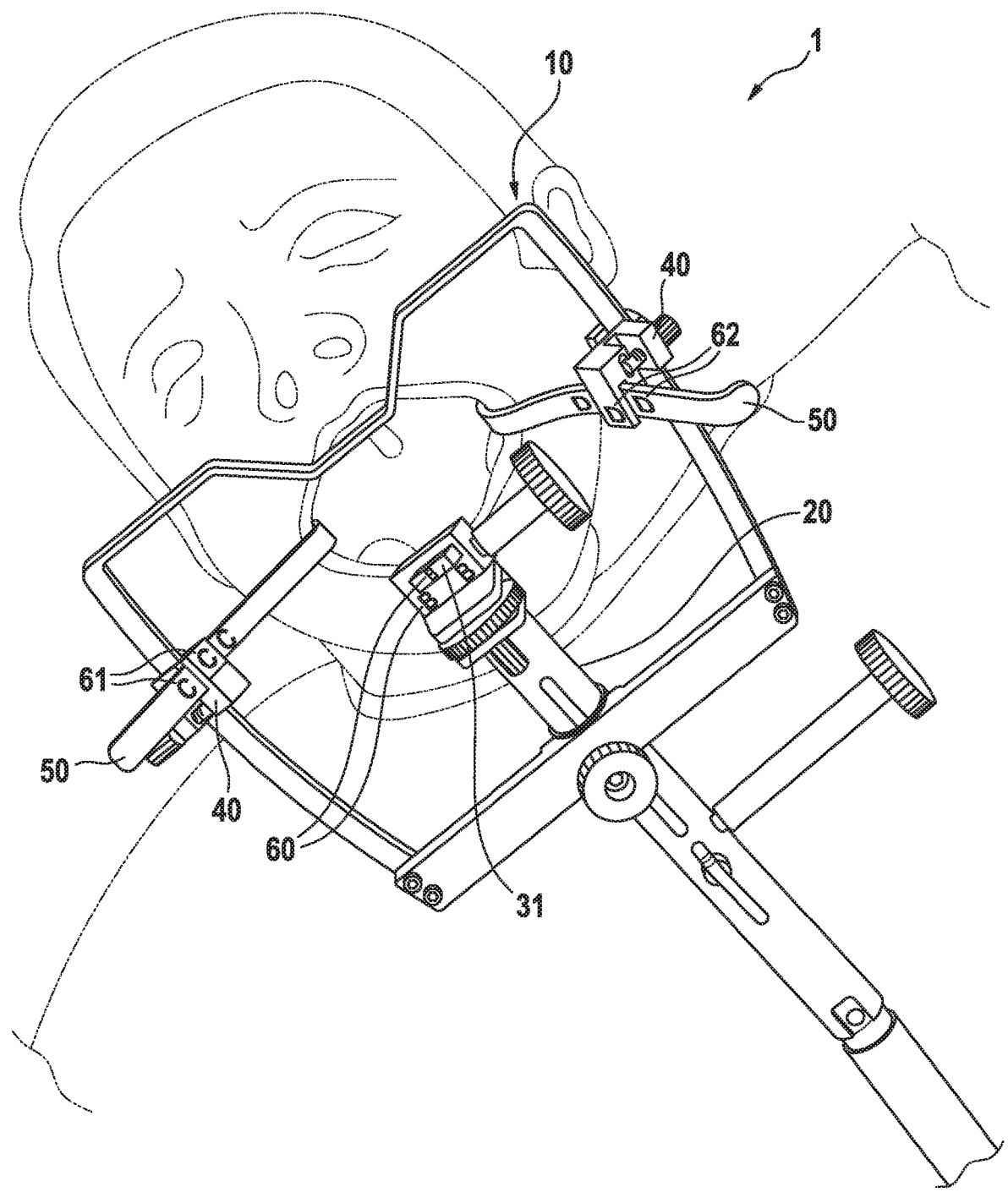

FIGS. 2a and 2b show a second laryngopharyngoscope retractor system 1, which substantially corresponds to that of FIGS. 1a and 1b, which is why reference is made to the explanations in that respect and the following only discusses the differences between the two embodiments.

Instead of color codes, the embodiment as per FIGS. 2a and 2b provides the codes 60-63 in the form of single-digit alphanumeric characters—specifically, individual letters. Here the letters are arranged in the respective for connecting two components 10, 20, 30, 40, 50 such that, in the case of the correct orientation of two components 10, 20, 30, 40, 50 to be connected, the alignment thereof corresponds.

Naturally, individual digits could also be used as a code 60-63 instead of individual letters.

FIG. 3 shows a third laryngopharyngoscope retractor system 1, which largely corresponds to that of FIGS. 1a, b, for example, including the code 60-63, which is why reference is made to the explanations provided above.

The laryngopharyngoscope retractor system 1 as per FIG. 3 is distinguished in that a multiplicity of different spatulas 30 are provided, which can be inserted alternatively into the spatula holder 20, as a result of which the laryngopharyngoscope retractor system 1 is usable in particularly flexible fashion.

Moreover, at least one auxiliary means adapter 70, which is releasably fastenable to the base frame 10, is provided, it being possible by means of said auxiliary means adapter to selectively fasten one of the auxiliary means 80 illustrated in FIG. 3—specifically, tumor grasping forceps 81 or smoke suction tube 82—to the base frame 10. Naturally, a plurality of auxiliary means 80 can be fastened to the base frame 10 at the same time with the aid of a plurality of auxiliary means adapters 70.

Each auxiliary means 80 is provided with a color code 64, which corresponds to a corresponding color code 64 on the auxiliary means adapter 70. In terms of its functionality, the color code 64 corresponds to the color codes 60-63 already discussed above. Since the two illustrated auxiliary means 81, 82 can be fastened to the base frame 10 using the same auxiliary means adapter 70, their respective code 64 has an identical color.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

What is claimed is:

1. A laryngopharyngoscope retractor system comprising:
a plurality of components including:
   a base frame with a coupling region and a spatula holder that is adjustable in terms of position and orientation by way of adjusting screws;
   a spatula that is releasably fastenable in the spatula holder;
   two cheek holder adapters that are releasably fastenable to the base frame; and
   two cheek holders, each of which is releasably fastenable to a respective cheek holder adapter,
wherein one or more of the base frame, the spatula holder, the spatula, the cheek holder adapter and the cheek holder of the plurality of components, in respective regions provided for the releasable connection to another one of the plurality of components, have a visible unique color code that corresponds to corresponding regions on the other of the plurality of components;
the plurality of components includes two components to be connected to one another, wherein the two components are connectable to each other in two or more orientations; and
the two components each having two differently colored codes, which set an orientation from the two or more orientations of each of the two components.

2. The laryngopharyngoscope retractor system of claim 1, further comprising:
   at least one auxiliary means adapter that is releasably fastenable to the base frame;
   at least one auxiliary means that is fastenable to the at least one auxiliary means adapter;
   wherein each of the at least one auxiliary means, in a region provided for the releasable connection, has a visible color code corresponding to corresponding regions on the at least one auxiliary means adapter.

3. The laryngopharyngoscope retractor system of claim 2, further comprising one or more additional auxiliary means having the same color code as the at least one auxiliary means.

4. The laryngopharyngoscope retractor system of claim 2, wherein the at least one auxiliary means is selected from a group consisting of a light carrier, a tumor grasping forceps, a suction tube for liquids and a smoke suction tube.

5. The laryngopharyngoscope retractor system of claim 1, further comprising an auxiliary means adapter provided for use with various auxiliary means, wherein the auxiliary means fitting to the auxiliary means adapter each have an identical code in regions provided for a connection to the auxiliary means adapter.

6. The laryngopharyngoscope retractor system of claim 1 further comprising one or more of additional spatulas having the same color code as the spatula and additional cheek holders having the same color code as the two cheek holders.

* * * * *